(12) United States Patent
Gerstner

(10) Patent No.: US 8,074,815 B2
(45) Date of Patent: Dec. 13, 2011

(54) MULTI-LEVEL RACK SYSTEM WITH ULTRAVIOLET LIGHT FOR SUPPORTING SURGICAL TOOLS

(76) Inventor: Jeffrey Gerstner, Honeoye Falls, NY (US)

( * ) Notice: Subject to any disclaimer, the term of this patent is extended or adjusted under 35 U.S.C. 154(b) by 777 days.

(21) Appl. No.: 12/126,572

(22) Filed: May 23, 2008

(65) Prior Publication Data
US 2009/0045154 A1 Feb. 19, 2009

Related U.S. Application Data

(60) Provisional application No. 60/931,936, filed on May 25, 2007.

(51) Int. Cl.
*A47B 43/00* (2006.01)
(52) U.S. Cl. ........ 211/193; 211/207; 108/108; 108/115; 362/125
(58) Field of Classification Search ............... 211/90.02, 211/90.04, 103, 190, 13.1, 187, 208, 168, 211/195, 175, 207, 134, 189, 192, 169, 165, 211/90.01, 196, 205, 150, 186, 193; 248/121, 248/122.1, 125.8, 291.1, 631, 239, 240, 240.3, 248/250; 108/147, 26, 23, 115, 108, 6, 116; 362/125, 133, 269; 280/47.35, 79.3, 33.991, 280/35, 47.24
See application file for complete search history.

(56) References Cited

U.S. PATENT DOCUMENTS

| | | | | |
|---|---|---|---|---|
| 1,554,137 A | * | 9/1925 | Slifkin | 108/6 |
| 2,982,419 A | * | 5/1961 | Shiels | 108/59 |
| 3,484,069 A | * | 12/1969 | Larson | 248/220.42 |
| 3,485,382 A | * | 12/1969 | Larson | 211/150 |
| 3,774,773 A | * | 11/1973 | Brent | 211/70.6 |
| 3,776,387 A | * | 12/1973 | Brent | 211/70.6 |
| 4,008,873 A | * | 2/1977 | Travaglio et al. | 248/242 |
| 4,035,938 A | * | 7/1977 | Neilsen | 40/379 |
| 4,441,433 A | * | 4/1984 | Caldwell | 108/152 |
| 4,473,963 A | * | 10/1984 | Hardy et al. | 40/651 |
| 4,572,594 A | | 2/1986 | Schwartz | |
| 4,776,472 A | * | 10/1988 | Rosen | 211/187 |
| 4,786,812 A | * | 11/1988 | Humphreys | 250/455.11 |

(Continued)

FOREIGN PATENT DOCUMENTS

DE 701336 C 1/1941

(Continued)

OTHER PUBLICATIONS

Random House College Dictionary, Copyright 1982 definition of "substainally", p. 1310.*

*Primary Examiner* — Darnell Jayne
*Assistant Examiner* — Devin Barnett
(74) *Attorney, Agent, or Firm* — George R. McGuire; David B. Woycechowsky

(57) ABSTRACT

A rack for use in an operating room during surgery to hold surgical instruments. The rack includes a vertical support (including an adjustable height portion); rack support braces; rack support arms; a base interface member; casters; a base; and lighted trays. The lighted trays radiate ultraviolet and/or visible light to provide visible light in low light conditions and/or to inhibit bacterial growth. The trays are detachably attachable from the rack support arms which helps the trays to be maintained in a sterile condition, even if the rest of the rack is not maintained in a sterile condition.

10 Claims, 16 Drawing Sheets

U.S. PATENT DOCUMENTS

| | | | | |
|---|---|---|---|---|
| 5,082,234 | A * | 1/1992 | Smith | 248/669 |
| 5,160,699 | A | 11/1992 | Siegal | |
| 5,170,804 | A | 12/1992 | Glassman | |
| 5,257,703 | A * | 11/1993 | Ascik et al. | 211/166 |
| 5,303,830 | A * | 4/1994 | Metcalf | 211/57.1 |
| 5,347,922 | A * | 9/1994 | Metcalf | 100/108 |
| 5,396,904 | A | 3/1995 | Hartigan, Jr. | |
| 5,439,122 | A * | 8/1995 | Ramsay | 211/187 |
| 5,443,168 | A * | 8/1995 | Dyment et al. | 211/149 |
| 5,526,941 | A * | 6/1996 | Ford | 211/59.1 |
| 5,839,589 | A * | 11/1998 | Hillard | 211/70.6 |
| 5,913,422 | A * | 6/1999 | Cote et al. | 206/370 |
| D423,671 | S * | 4/2000 | Garito et al. | D24/185 |
| 6,164,738 | A * | 12/2000 | Dane et al. | 312/311 |
| 6,189,459 | B1 | 2/2001 | DeAngelis | |
| 6,276,810 | B1 * | 8/2001 | Vosshenrich | 362/127 |
| 6,331,280 | B1 * | 12/2001 | Wood | 422/300 |
| 6,493,220 | B1 * | 12/2002 | Clark et al. | 361/679.41 |
| 6,702,126 | B2 * | 3/2004 | Park | 211/59.1 |
| 6,702,128 | B2 * | 3/2004 | Winig et al. | 211/90.01 |
| 6,823,999 | B2 * | 11/2004 | Heneveld, Sr. | 211/87.01 |
| 7,159,728 | B2 * | 1/2007 | Smith | 211/166 |
| 7,168,715 | B1 * | 1/2007 | Friedman | 280/47.35 |
| D553,324 | S * | 10/2007 | Lieblein et al. | D34/14 |
| 7,314,143 | B1 * | 1/2008 | Johnson | 211/106 |
| 7,350,649 | B1 * | 4/2008 | Martens | 211/90.02 |
| D580,193 | S * | 11/2008 | Sparkowski | D6/463 |
| 7,533,777 | B2 * | 5/2009 | Winkler | 211/201 |
| 7,546,990 | B1 * | 6/2009 | McGuire | 248/111 |
| 7,631,773 | B1 * | 12/2009 | Calabrisotto et al. | 211/196 |
| D626,238 | S * | 10/2010 | Zinnanti | D24/185 |
| 7,871,176 | B2 * | 1/2011 | Kelly et al. | 362/126 |
| 7,871,581 | B1 * | 1/2011 | Coleman et al. | 422/300 |
| 2001/0054862 | A1 * | 12/2001 | Cinese | 312/249.8 |
| 2002/0192731 | A1 * | 12/2002 | H. Shih | 435/7.92 |
| 2003/0034459 | A1 | 2/2003 | Bonin | |
| 2004/0040922 | A1 * | 3/2004 | Ko | 211/153 |
| 2004/0101456 | A1 | 5/2004 | Kuroshima et al. | |
| 2006/0260515 | A1 | 11/2006 | Hodges et al. | |
| 2007/0295681 | A1 * | 12/2007 | Colin | 211/90.03 |
| 2009/0001038 | A1 * | 1/2009 | Zimmer | 211/135 |

FOREIGN PATENT DOCUMENTS

EP      1905343 A1      4/2008

* cited by examiner

MULTI-LEVEL RACK SYSTEM WITH ULTRAVIOLET LIGHT FOR SUPPORTING SURGICAL TOOLS

RELATED APPLICATION

The present application claims priority to U.S. provisional patent application No. 60/931,936, filed on May 25, 2007; all of the foregoing patent-related document(s) are hereby incorporated by reference herein in their respective entirety(ies).

BACKGROUND OF THE INVENTION

1. Field of the Invention

The present invention relates to cabinets, racks and shelving, more particularly to cabinets, racks and shelving for medical applications, and even more particularly to cabinets and shelving for operating rooms to be used during surgery.

2. Description of the Related Art

It is conventional to use carts and shelves in an operating room during surgery. U.S. Pat. No. 4,572,594 ("Schwartz") discloses an arthroscopy support stand including a wheel mounted steel cabinet and shelves (open at the front) for supporting various arthroscopic surgery appliances, a vertical support column and a pair of vertically-spaced support arms. The arms are pivotally mounted at the middle of the cabinet so that the support column can be shifted back and forth across the front of the cabinet.

U.S. Pat. No. 6,189,459 ("DeAngelis") discloses an auxiliary shelf that can be attached to an operating room cart to provide additional sterile space for instruments during surgery. The auxiliary shelf can be rotated between a horizontal position, for use as a shelf, and a collapsed position parallel along the back of the cart. The collapsed position permits the cart and DeAngelis shelf and cart assembly to be stored in less space. The DeAngelis shelf and cart assembly also includes a mounting clamp, shelf leg, holes and a pin so that the shelf position is adjustable in the vertical direction.

U.S. Pat. No. 5,160,699 ("Siegal") discloses an enclosed sanitizing cabinet for exposing eyewear articles to ultraviolet radiation from a fluorescent ultraviolet lamp. the lamp extends substantially the entire height of the cabinet. The cabinet includes shelf-forming rod members spaced and configured to support eyewear articles in such manner that the surfaces of the eyewear which contact a user's skin are exposed to ultraviolet radiation.

US published patent application 2003/0034459 ("Bonin") discloses a sanitization cabinet including an ultraviolet lamp mounted in the cabinet. the ultraviolet lamp heats and sanitizes air that is circulated through the Bonin cabinet.

US published patent application 2006/0260515 ("Hodges") discloses a modular sterilizable surgical table adapted for use during surgery in a hospital operating room. In the Hodges table, sterilizable sleeves are detachably attachable to posts. Sterilizable shelves are detachably attachable to the sleeves. the shelves have lips to help retain items on the shelf. The Hodges table is disclosed to include means for adjustably tilting one of the shelves. A back shelf is disclosed to be adjustable in the vertical direction.

Description Of the Related Art Section Disclaimer: To the extent that specific publications are discussed above in this Description of the Related Art Section, these discussions should not be taken as an admission that the discussed publications (for example, published patents) are prior art for patent law purposes. For example, some or all of the discussed publications may not be sufficiently early in time, may not reflect subject matter developed early enough in time and/or may not be sufficiently enabling so as to amount to prior art for patent law purposes. To the extent that specific publications are discussed above in this Description of the Related Art Section, they are all hereby incorporated by reference into this document in their respective entirety(ies).

BRIEF SUMMARY OF THE INVENTION

The present invention is directed to various designs for a cabinet for use in the operating room during surgery to hold instruments. Preferred features for the designs of the present invention include the following:

(1) multi-level rack design with disposable trays;
(2) mobile rack units allow for customized room set-up based on procedure and instrument requirements;
(3) mobility for easy movement of the racks from room to room for various reasons;
(4) removable plastic sterile trays that are easily set up, broken down, stored and/or handled;
(5) luminescent trays illuminate instruments during low light procedures;
(6) luminescent trays that irradiate the instruments in ultraviolet ("UV") light to inhibit bacteria growth;
(7) light source (for example, a UV light source") incorporated into the interior of the rack arms;
(8) trays with louvers built into the underside of the tray to allow light to travel through the tray while maintaining sterile integrity between the sterile tray and the non-sterile rack arms;
(9) sterile rack includes has a sterile plastic casing;
(10) sterile rack allows for customizable options, such as name, procedure numbers, etc.
(11) adjustable rack height provided by a pneumatic cylinder for technician or surgeon comfort and/or visual preferences;
(12) adjustable rack arm angle for technician or surgeon comfort and/or visual preferences;
(13) rack arms fold into a down position for easy storage when not in use;
(14) mechanism to connect racks to each other to form a semi-circle around technician or surgeon and allow additional racks to be added inter-operatively;
(15) rack may be designed to support 100 pounds (lbs.) or more per tray level;
(16) rack with lowest tray level at 36 inches over ground level; and/or
(17) rack with approximately 14-16 inches of clearance between adjacent tray levels.

Various embodiments of the present invention may exhibit one or more of the following objects, features and/or advantages:

(1) reduces or eliminates need for sterile cloth drapes to cover stainless steel tables;
(2) helps organize equipment trays with good accessibility of instruments;
(3) reduces occurrence of situations where instruments are lost or misplaced due to a disorganized surgical room set-up;
(4) allows accessible and organized surgery room storage of hundreds of instruments;
(5) prevents instrument trays from being "stacked" together during long surgical procedures and associated risk of bacteria growth;
(6) reduces or eliminates sterile field violations due to lack of floor space in sterile working area;
(7) helps reduce hospital infection rate; and/or
(8) improved portability, instrument work space, efficiency, safety and/or standardization.

According to one aspect of the present invention, an operating room rack system includes a rack assembly and a detachably attachable tray unit. The rack assembly includes a base, a vertical support, and a set of arm(s). The vertical support is mechanically connected (see DEFINITIONS section) to the base and extends upwardly from the base. The set of arm(s) extends from the vertical support. The tray unit is detachably attachable to the set of arm(s) and adapted so that when the tray unit is detachably attached to the set of arm(s), the tray unit will remain in a sterile condition even when the rack assembly is not maintained in a sterile condition.

According to a further aspect of the present invention, an operating room rack system includes a base, a vertical support, a rack support brace, an arm rotating device and a set of arm(s). The vertical support is mechanically connected to the base and extends upwardly from the base. The rack support brace defines an interior space and is mechanically connected to the vertical support. The arm rotating device defines a rotation axis. The arm rotating device is located at least partially within the interior space of the rack support brace. The set of arm(s) is mechanically fixed to the arm rotating device. The arm rotating device and the set of arm(s) are rotatable about the rotation axis between an up position and a down position. The set of arm(s) is adapted to engage with a tray unit in a detachably attachable manner.

According to a further aspect of the present invention, an operating room rack system includes a vertical support frame, a first shelf and a first light source. The vertical support frame includes at least a first vertical support member. The first shelf has a first supporting surface. The first supporting surface extends from the vertical support frame. The first shelf is located and oriented so that the first supporting surface is at an angle appropriate for supporting surgical instruments. The first light source is mechanically connected to the rack system. The first light source is located and oriented so that it irradiates at least a portion of the first supporting surface with light (see DEFINITIONS section).

BRIEF DESCRIPTION OF THE DRAWINGS

The present invention will be more fully understood and appreciated by reading the following Detailed Description in conjunction with the accompanying drawings, in which.

DETAILED DESCRIPTION OF THE INVENTION

Figure 5:
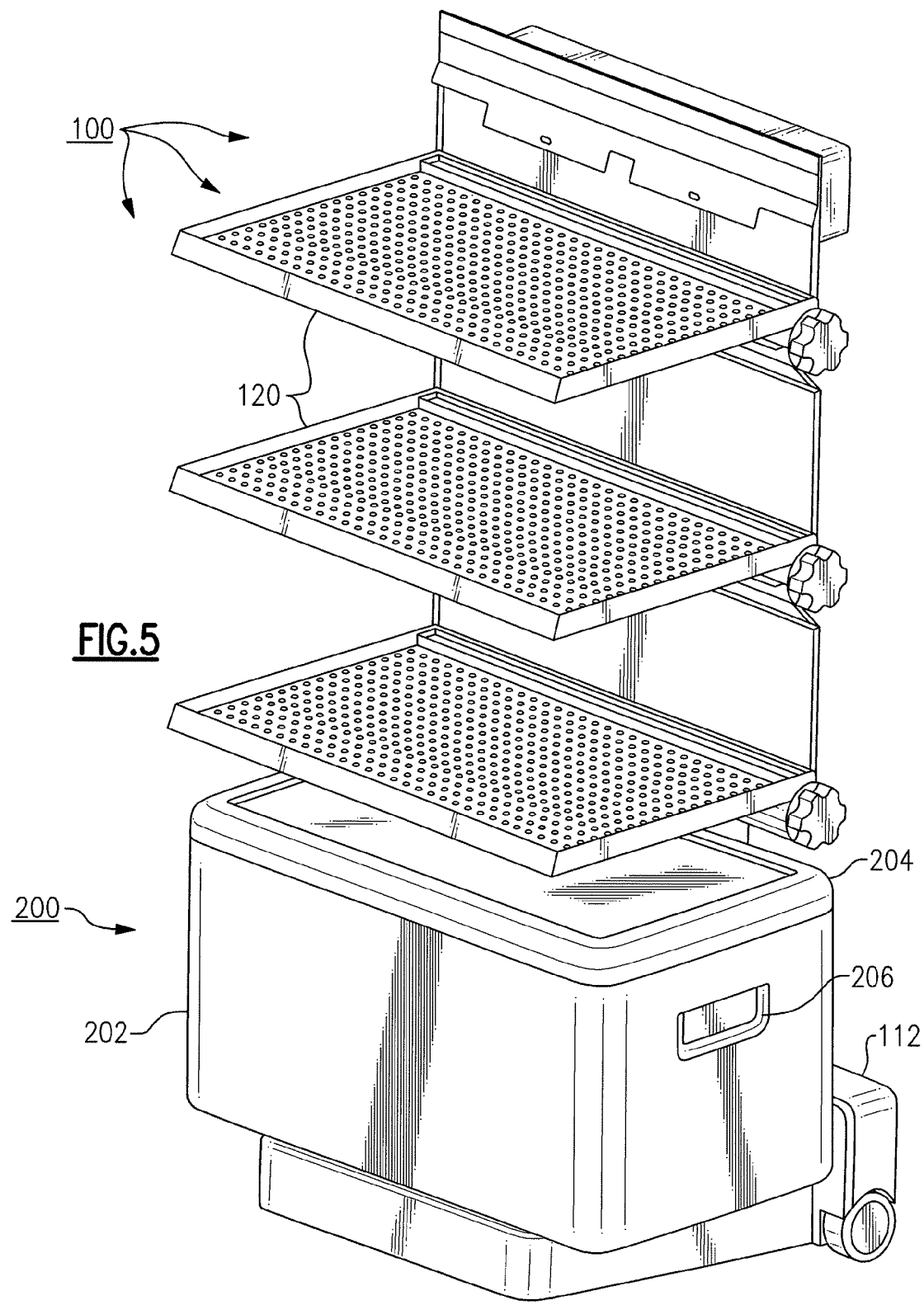
FIG. 5 is a perspective view of the first embodiment rack with the trays in place and a storage container resting on the base.
Figure 6:
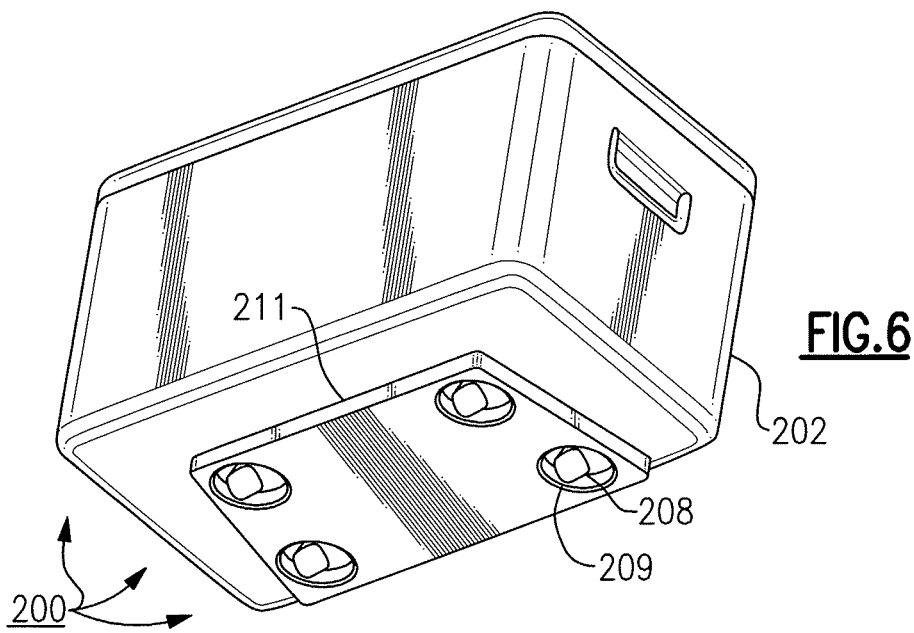
FIG. 6 is a perspective view of the storage container showing its bottom surface.
Figure 7:
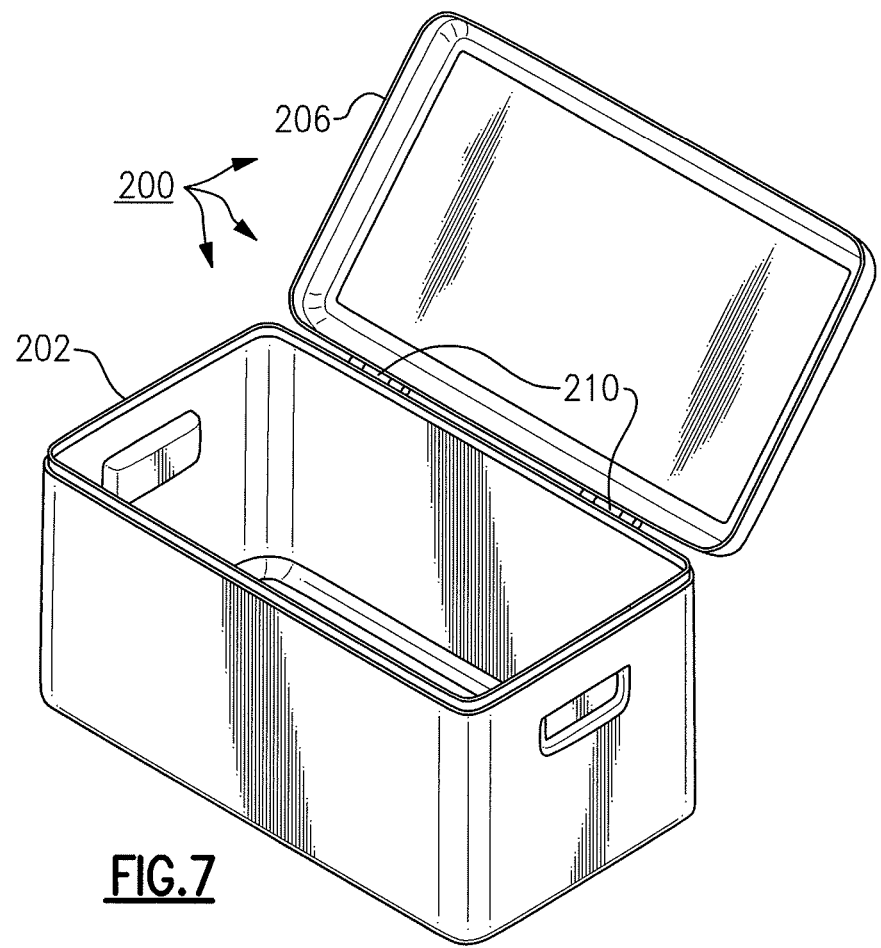
FIG. 7 is a perspective view of the storage container with its lid in the open position.

Rack 100 is an exemplary embodiment of the present designed for use in an operating room during surgery to hold surgical instruments. As shown in FIGS. 1 to 20, rack 100 includes: vertical support 102; rack support braces 104; rack support arms 106; arm rotating knob 108; height adjustment device 110; base interface member 112; casters 114; base 116; header 118; and lighted trays 120, 122. Header 118 and lighted trays 120, 122 are easily removable from the rest of the rack assembly 100. As shown in FIGS. 5 to 7, rack 100 may also be used with storage container 200, including main body 202; lid 204; handles 206; casters 208; caster recesses 209; hinges 210 and protrusion 211.

Figure 1:
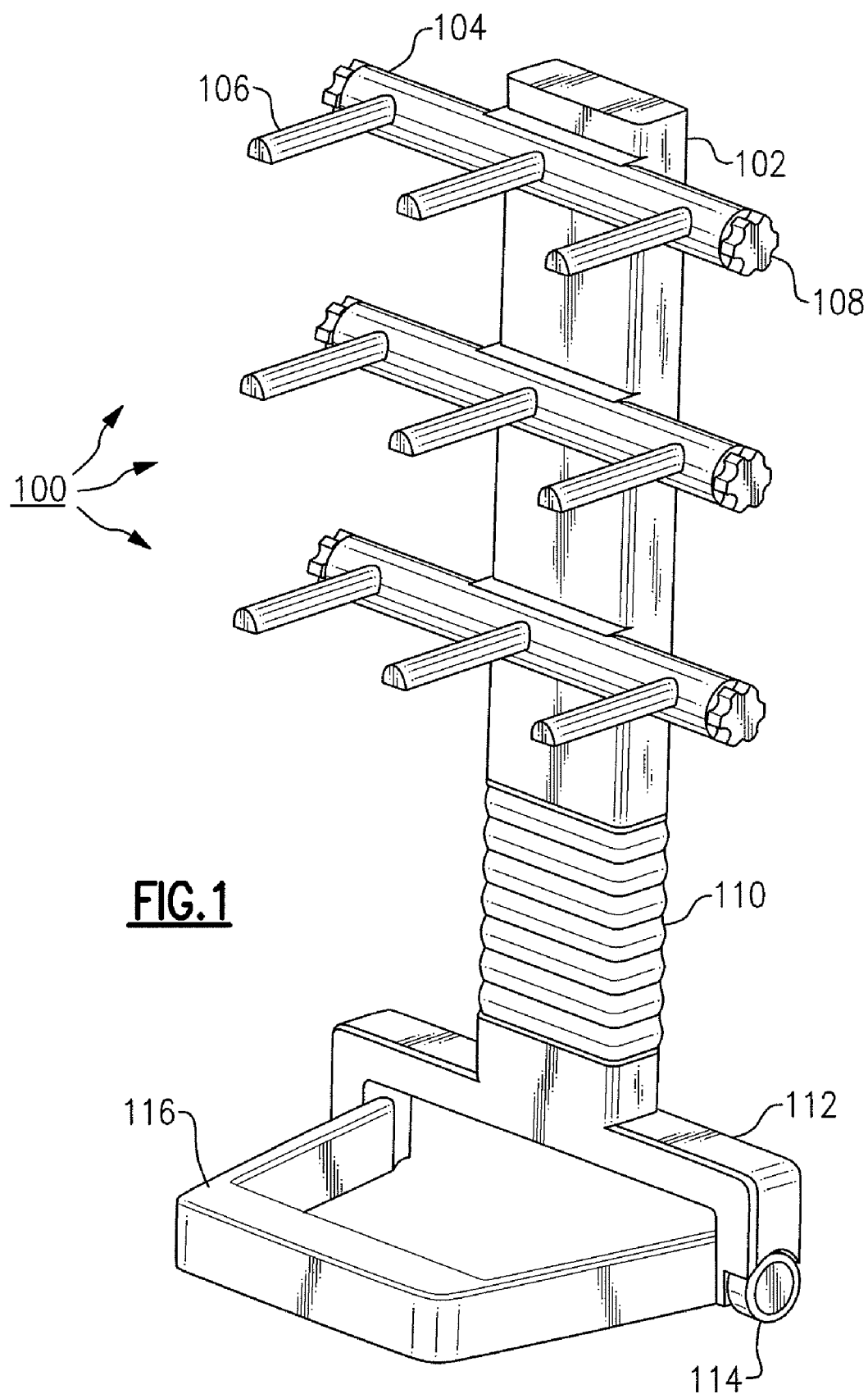
FIG. 1 is a perspective view of a first embodiment of a rack according to the present invention with the trays removed and the tray arms in the horizontal position.

As shown in FIG. 1, exemplary rack 100 has three rack support braces 104, with each elongated, cylindrical rack support brace having: (i) an arm rotating knob 108 at one axial end; and (ii) a set of three parallel, spaced apart rack support arms 104 extending from it in the radial direction. A user can rotate the arm rotating knob to turn the rack support brace about its central axis and thereby rotate the set of arms fixed to the rack support brace. As will be shown below, this rotation of the arms allows adjacent racks to nest in a space-efficient manner in a front to back stack arrangement.

Many variations on this basic design are possible, although perhaps not preferred. Some (not all) possible variation will now quickly be mentioned to help evoke the full scope of various aspects of the present invention. There may be more or fewer than three rack support braces. A rack support brace may have fewer or more than three arms. The arm(s) may have a different geometry than what is shown in FIG. 1, such as being more sheet shaped, shaped as I-beams, shorter, wider, etc.). There may be more than one vertical support. The vertical support may have a different geometry (for example, substantially planar or sheet shaped or cylindrical). Although less preferred, the rotatability of the rack support brace and arms could be omitted entirely in some embodiments of the present invention. The rack support braces could be designed to rotate in the horizontal plane, especially if the vertical support is cylindrical. The rack support braces could be made independently vertically adjustable. The knob could be shaped differently or omitted entirely.

Preferably, the arms are molded straight with an engineering resin, or insert injection molded with a metal flat bracket inside/embedded in the arm. Preferred materials for making the arms include polycarbonate or a glass filled nylon. Preferably, the arm(s) are mechanically attached to the rack support brace along with mechanical fit/connection points.

Figure 3:
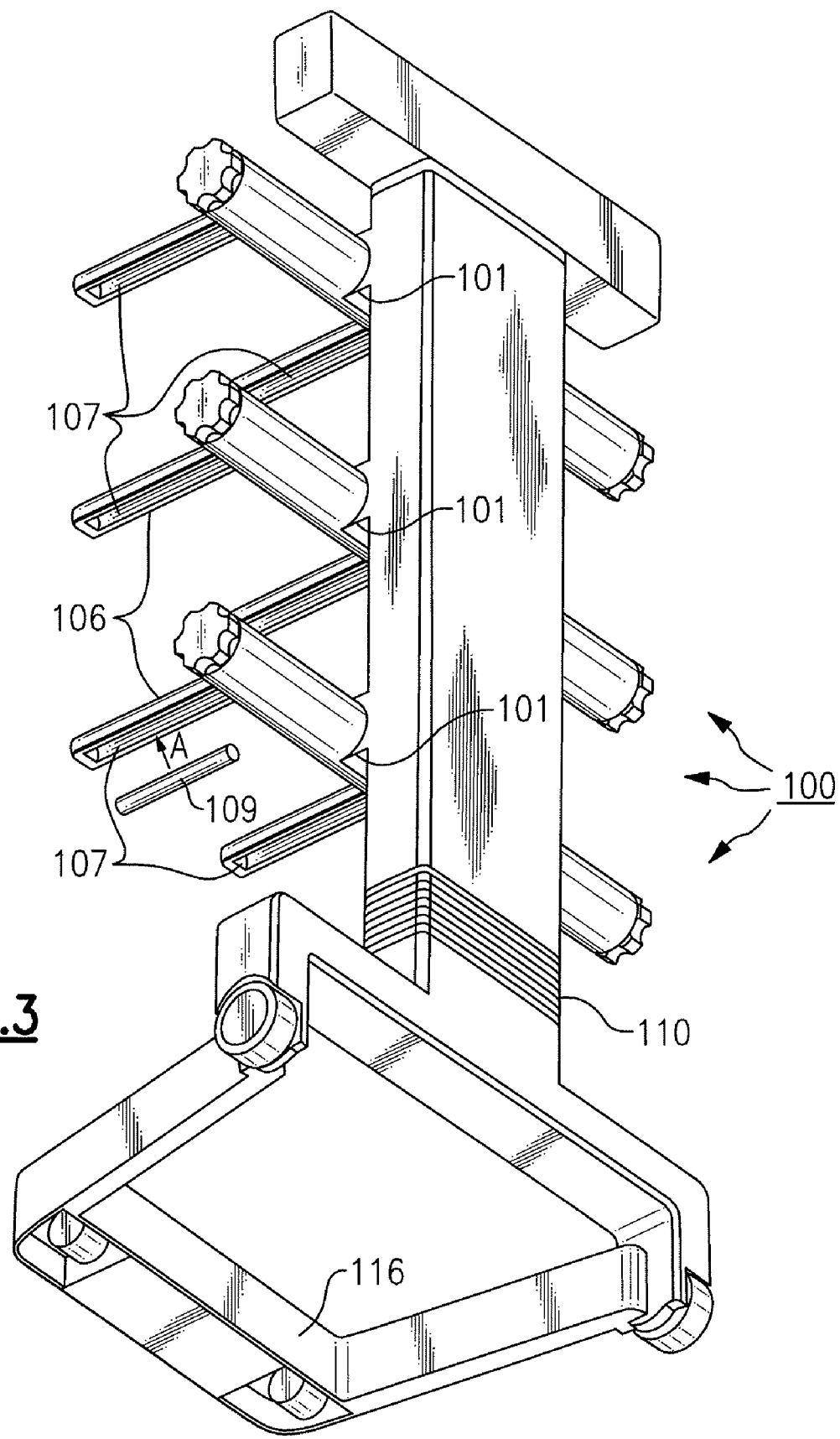
FIG. 3 is a perspective view of the first embodiment rack.

The rack support brace is preferably made out of cast metal or a high density aluminum casting. Preferably, it is mechanically attached to the vertical support along with mechanical fit/connection points. Turning attention to FIG. 3 at bearings 101, the bearings extending from the vertical support are only shown as extending about 180 degrees around the rack support braces. This is not necessarily preferred and the bearings may extend, for example, 360 degrees around the rack support braces. Importantly, the rotatable mechanical connection between the vertical support and support braces may be any type of rotatable mechanical connection now known or to be developed in the future.

Figure 2:
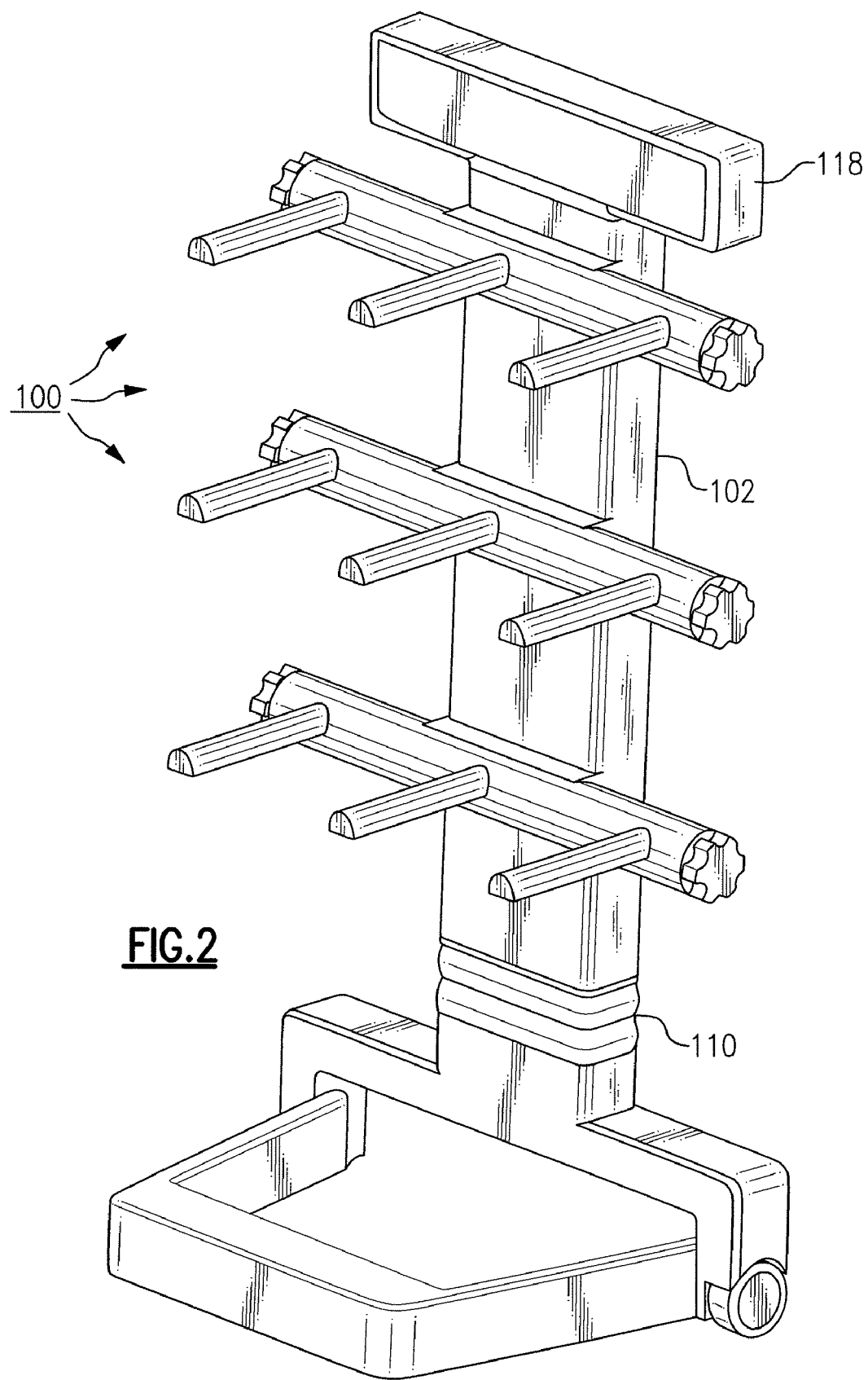
FIG. 2 is a perspective view of the first embodiment rack with the trays removed and a header in place.

FIG. 2 shows rack 100 with header 118 in place on the top surface of the vertical support. Comparing FIG. 1 to FIG. 2, it can be seen that height adjustment device is vertically adjustable between the extended position of FIG. 1 and the compressed position of FIG. 2. Preferably the height adjustment device includes a pneumatic device within a bellows style housing, but other types of height adjustment devices are also possible. In some embodiments of the present invention, the height adjustment device may be omitted. It is preferable to have a height adjustment device because: (i) the height of the lighted trays can be adjusted for comfort and visibility; (ii) the amount of space between the base and the lowest tray can be adjusted so that objects can be placed on the base (see FIG. 5); and (iii) the overall height of the rack can be reduced for storage in low-ceilinged areas and the like.

Header 118 can be used, for example, for identification of a set of tools/implants, or for doctor-specific branding.

The height adjustment device is preferably a pneumatic device, but could be any type of height adjustment device now known or to be developed in the future. A pneumatic device would preferably be activated by a foot pedal extension off of the base. The bellows skin is preferably made of injection molded engineering resin.

FIG. 3 shows the back side of rack 100. In this view it can be seen how base 116 is shaped so that it allows close nesting with adjacent racks in a front to back stack (see also FIG. 10). FIG. 3 also shows an important feature of some embodiments of the present invention which is recess and mounting hardware 107, which is built into the underside of each arm 106. The recess and mounting hardware is shaped and sized to accommodate a light source (see DEFINITIONS section) 109. The light source is inserted into recess in the direction of arrow A. Preferably, the light source irradiates visible light radiation so that objects on the lighted trays and/or in vicinity of the rack may be seen clearly, even in low light operating conditions. Preferably, the light source irradiates UV radiation to inhibit bacteria growth on the lighted trays and/or on objects placed on the lighted trays.

The light source preferably receives its electrical power through hardwired connections made up of UL components for powering off of circuit in the operating room ("OR"). Conduits for wiring are preferably built inside of the unit housing/column. Various kinds of bulbs may be used for the light source including, but not limited to, halogen, neon and/or incandescent. Their may be various types of mechanical connection between the bulb or bulb assembly and the arm, including but not limited to, slide in, screw in, quick release and/or friction fit.

Figure 4:
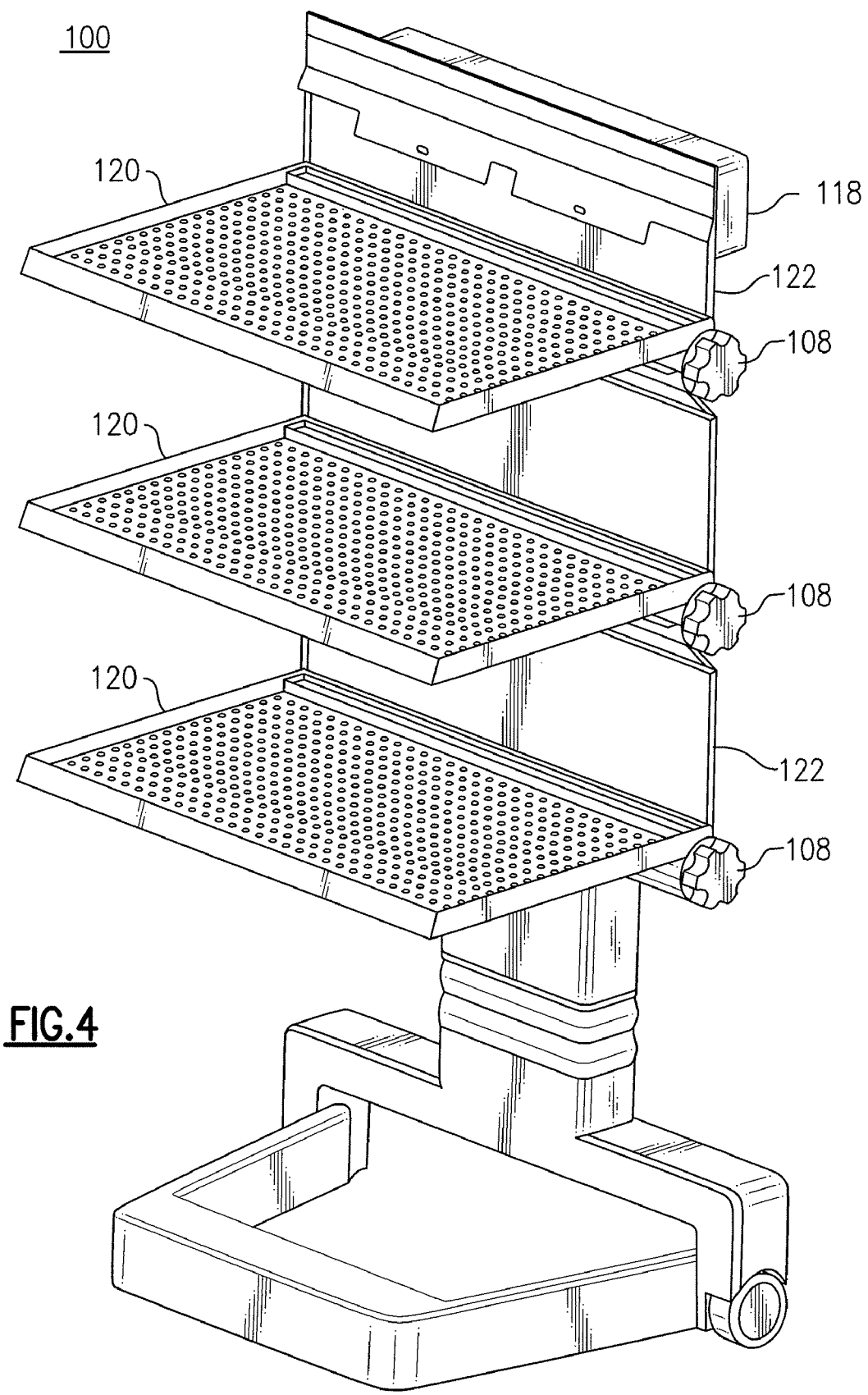
FIG. 4 is a perspective view of the first embodiment rack with trays in place.

FIG. 4 shows rack 100 with detachably attachable lighted trays 120, 122 attached, with one lighted tray being attached across each set of arms 106. The exploded view of FIG. 8 helps give an idea how each lighted tray is secured by a set of arms. As shown in FIG. 4, lighted trays 120, 122 include hinged cover 122 and tray top 120. Each tray top includes a surgical instrument supporting surface. When the lighted trays are separated from the rack assembly: (i) the lighted trays can be washed, sterilized, or even disposed of; and the rest of the rack can be stored with other racks in a space-efficient manner (see FIG. 10). When a surgical operation is to be performed, the sets of arms are rotated into the up position (or perhaps an angled position) and a lighted tray is slid onto each set of engaging arms. Once the trays are in place, surgical tools can be stored on the tray supporting surfaces in an organized manner.

Covers 122 preferably help provide for sterile Field requirements. The covers are preferably made of injection molded non-engineering resin. The covers preferably include "living hinges" so that they can fold down for the racks to "stack and store" in a space efficient manner. Tray tops 120 are preferably made of injection molded non engineering resin. Preferably, the trays are one time use items for sterilization reasons. Preferably the trays are sterilized to any applicable codes at the clean-room assembly and packing facility prior to shipping to the surgical centers.

Once the trays are in place, surgical tools can be stored on the tray supporting surfaces in an organized manner during surgery. Because of the engagement between the arms and the lighted trays, the trays remain sterile, even when the arms and the rest of the rack assembly is not sterile. Of course, in embodiments of the present invention with UV lights, that helps maintain the tray tops in a more sterile state, even as organic matter and residues build up as surgical tools are used during surgery.

The arms preferably hold the tray tops securely because trays will slide over and snap into the tray arms via mechanical snap detail. The trays will snap/lock/engage in place to prevent accidental dislodgement and the like. Any non-sterile conditions at the surfaces of the arms and the vertical support will not spread to the supporting surface of the trays because the sterilized tray will cover the arms and keep the supporting surface away from the vertical support. Preferably, the tray is discarded after use because it is generally better to provide a fresh sterilized tray than to sterilize a used tray.

FIG. 5 shows rack 100 with storage container 200 resting on its base. As shown in FIG. 6, protrusion 211 is shaped so that the storage container can be secured within base 116.

The storage container is used to store tools, instruments, etc. Preferably, the storage container is kept in a sterile condition. Preferably, the lowest tray can be raised high enough so that the hinged lid of the storage container can be opened when the storage container is sitting on the base.

Figure 8:
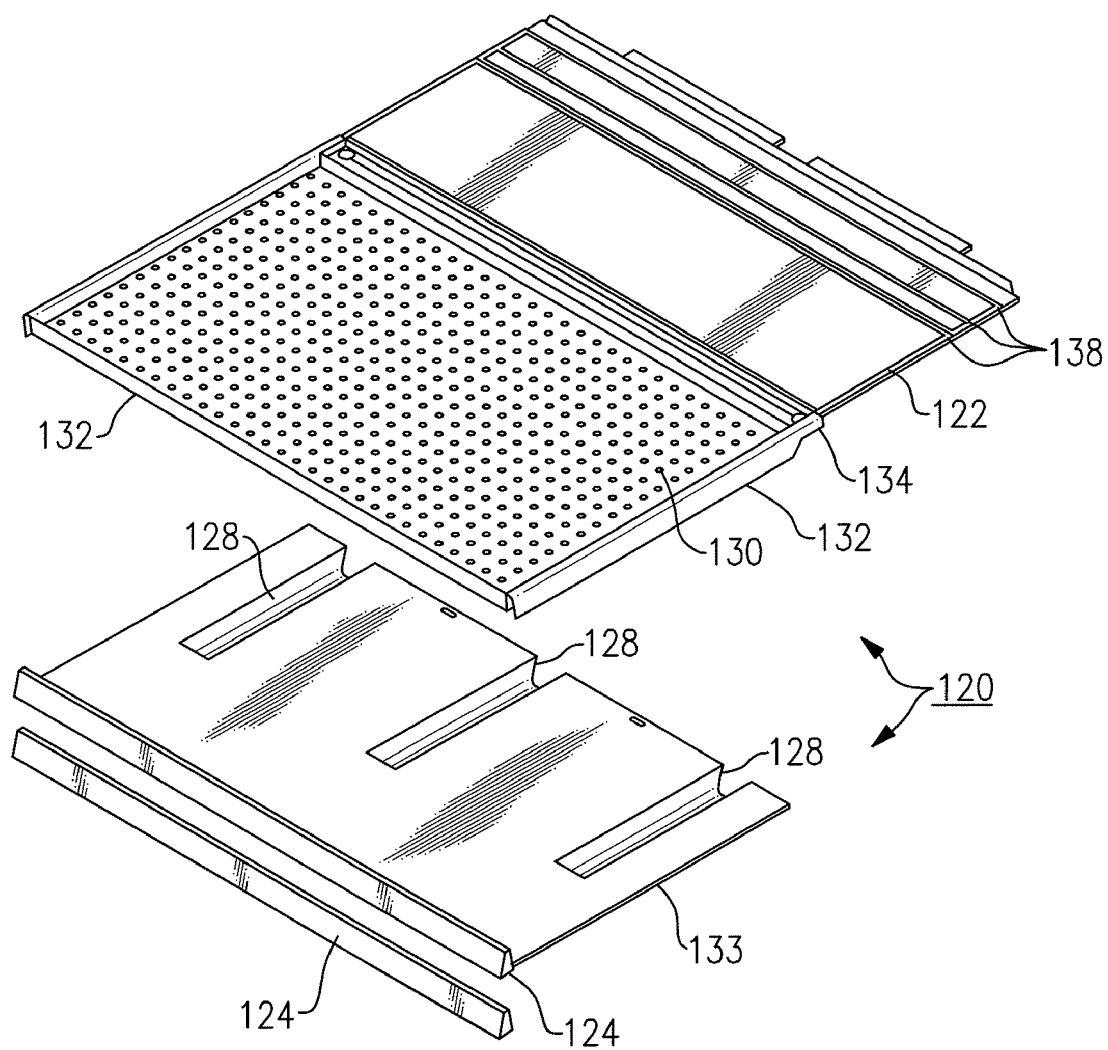
FIG. 8 is a perspective exploded view of a tray for use with the first embodiment rack.
Figure 9:
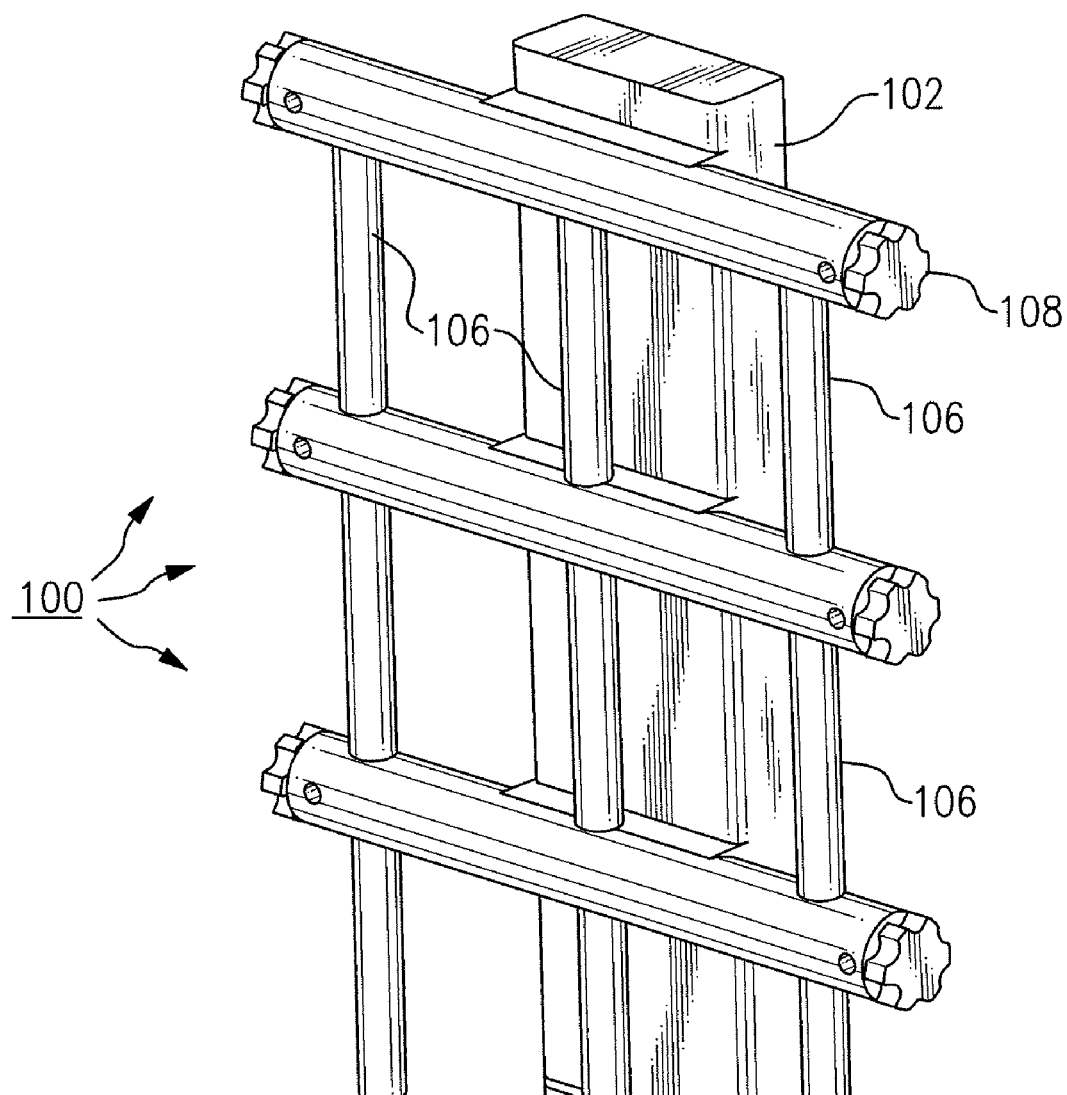
FIG. 9 is a perspective view of the first embodiment rack with the trays removed and the tray arms in the vertical, or down, position.
Figure 10:
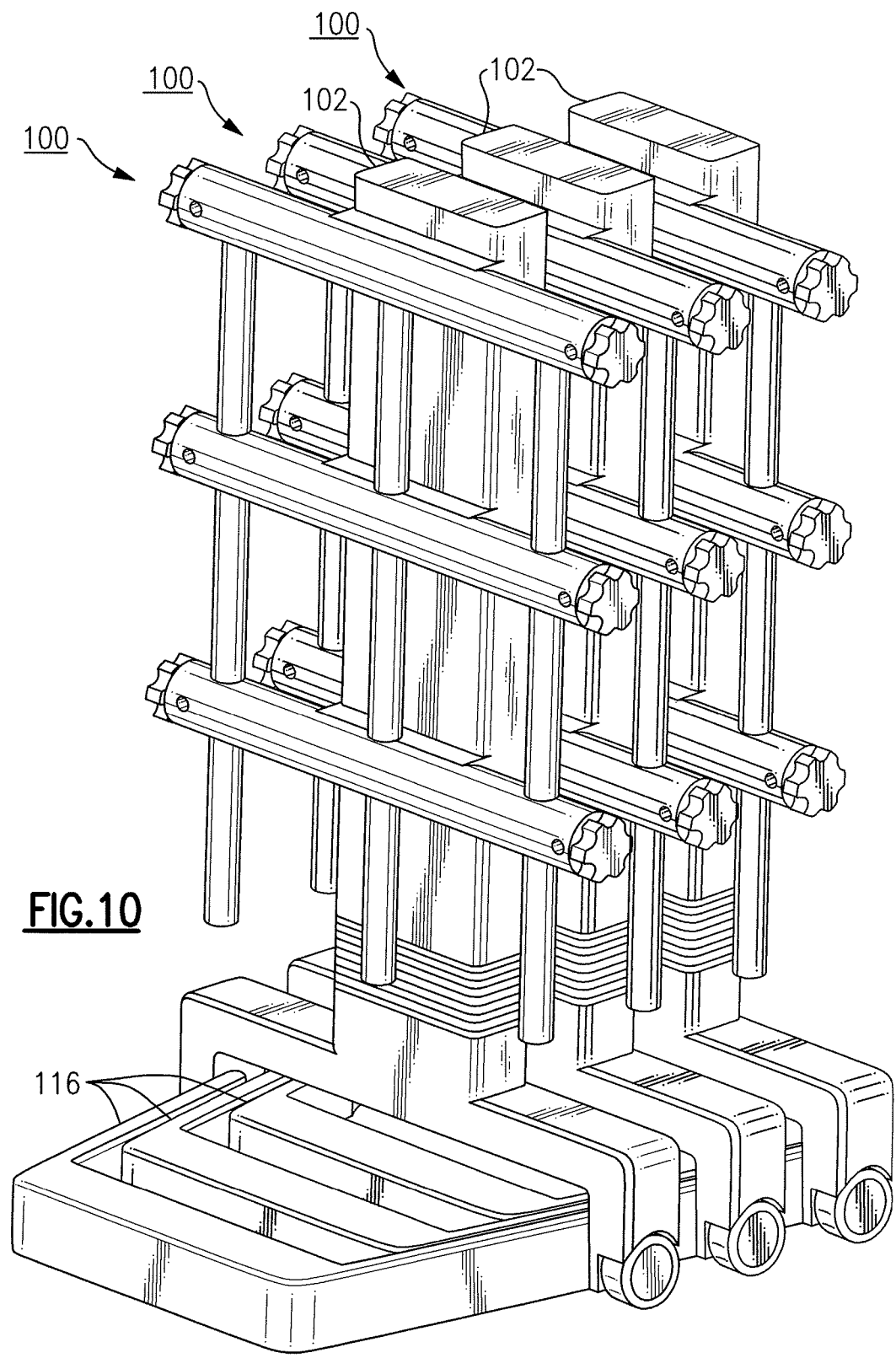
FIG. 10 is a perspective view of three first embodiment racks nested together for storage.

FIG. 8 shows lighted tray 120, 122 including art insert 124, upper tray top member 130, lip 132, lower tray top member 133, cover hinge 134 and living hinges 138. The art insert may be used as a surface for bearing printed materials, such as procedure numbers, doctor identification and/or patient identification. The upper tray top member has a top surface which is the supporting surface for the surgical tools. As shown in FIG. 8, the upper tray top member preferably includes holes to accept driver/locater inserts (not shown). The lip is sized to help keep surgical tools from accidentally falling off the supporting surface, while still allowing easy access to the tools. The lower tray top member includes recesses 128 for the arms 106 and light sources 109 (see FIG. 3). The cover hinge allows the cover to pivot between an open position (see FIG. 4 and FIG. 8) and a closed position (see FIG. 13 and FIG. 16).

Light escapes from inside recesses 128 because tray bottoms are molded in a clear, UV resistant resin. Light leaves recesses 128 over the entire half round area of 128 (allowing light to be transmitted directly down onto the items on the tray below.

Figure 11:
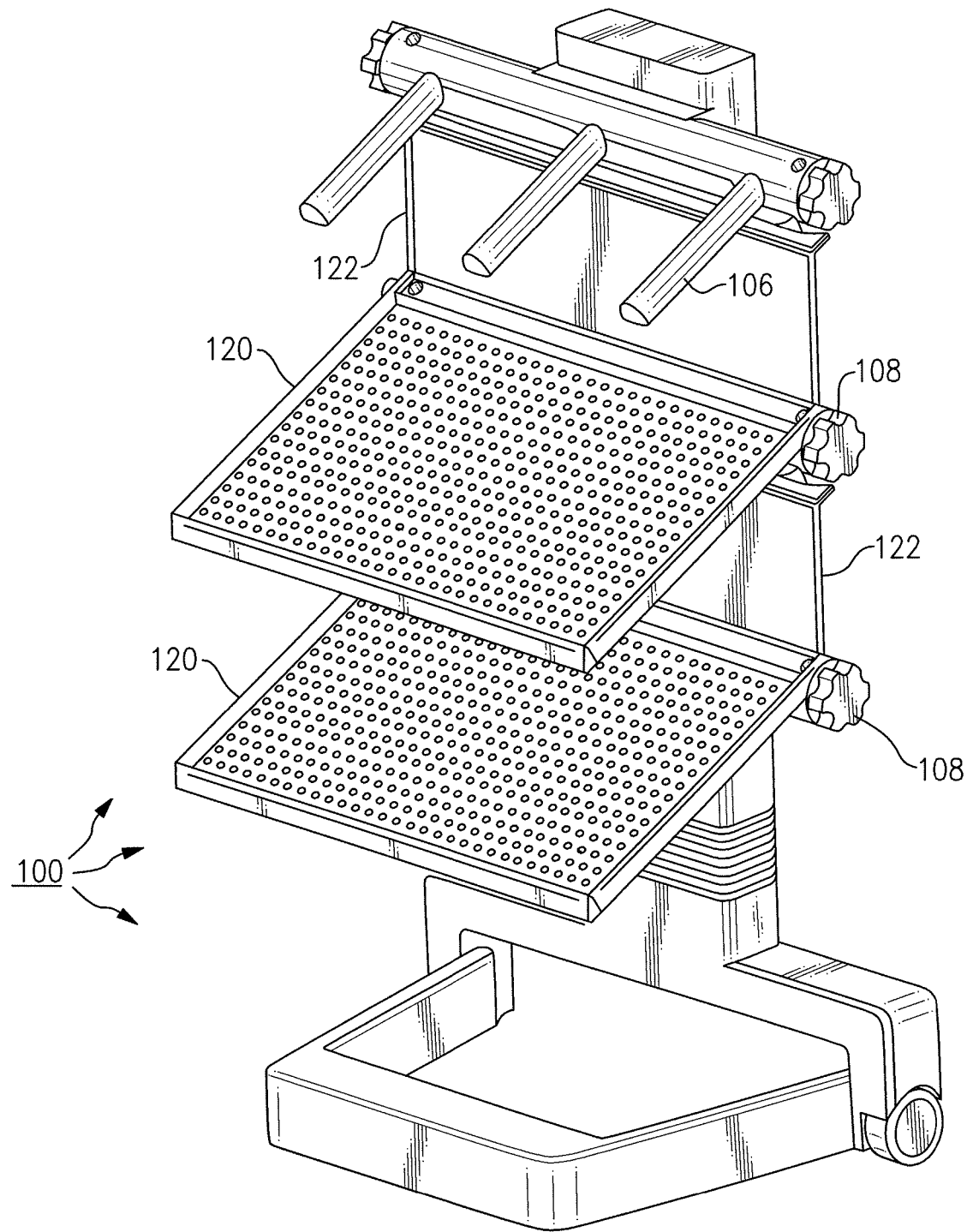
FIG. 11 is a perspective view of the first embodiment rack with some of the trays in place and its tray arms at an intermediate angular position.
Figure 12:
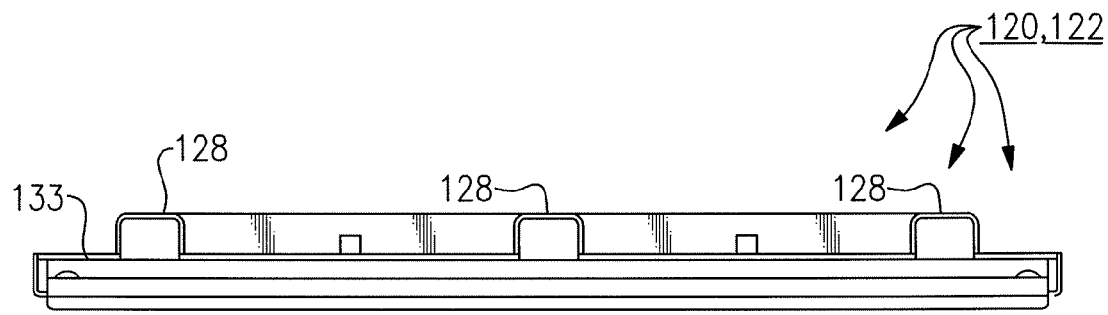
FIG. 12 is an orthographic back view of the tray.
Figure 13:
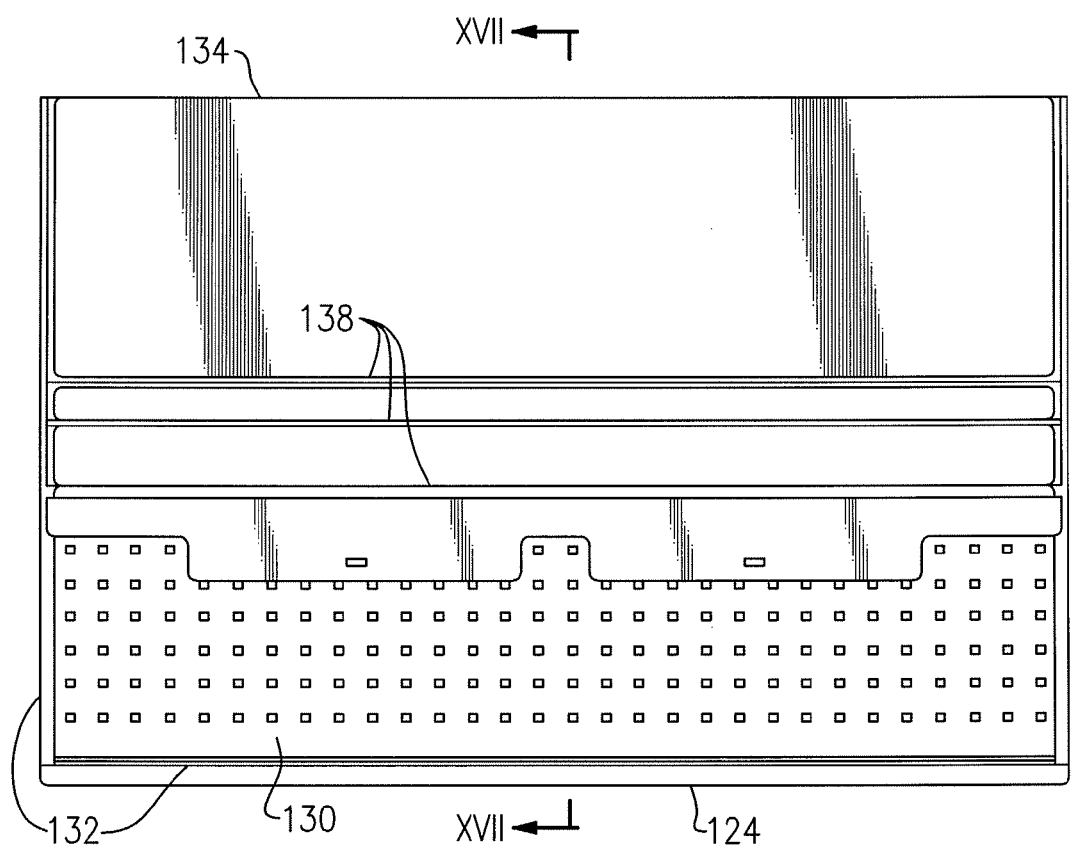
FIG. 13 is an orthographic top view of the tray.
Figure 14:
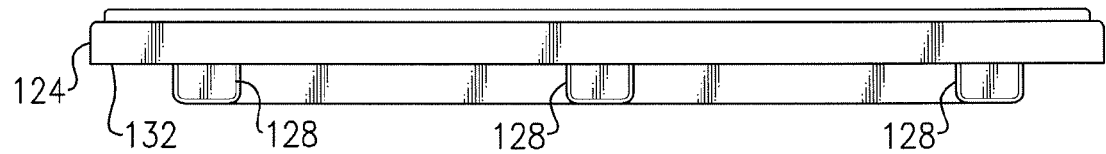
FIG. 14 is an orthographic front view of the tray.
Figure 15:
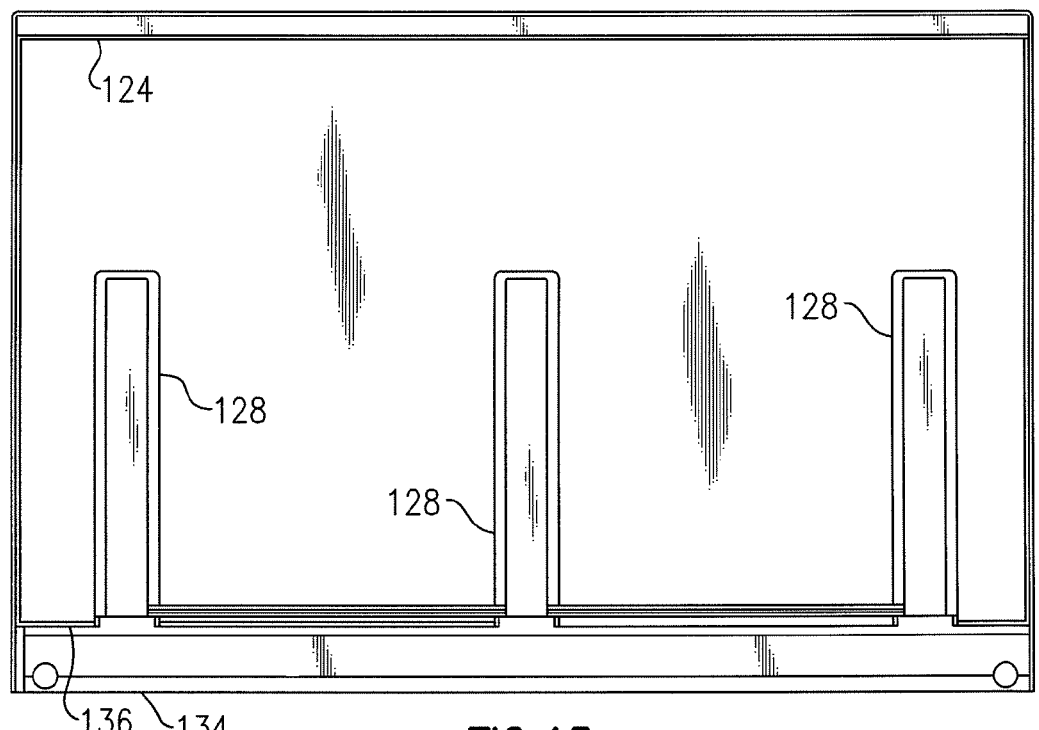
FIG. 15 is an orthographic bottom view of the tray.
Figure 16:
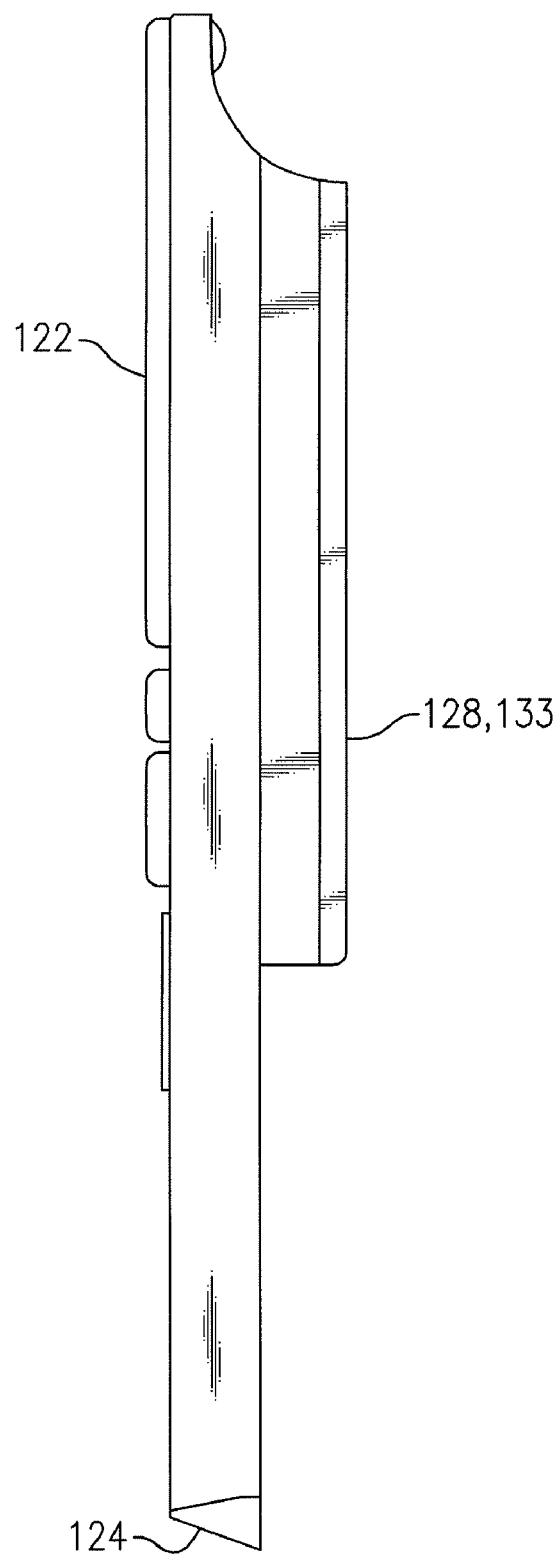
FIG. 16 is an orthographic side view of the tray.
Figure 17:
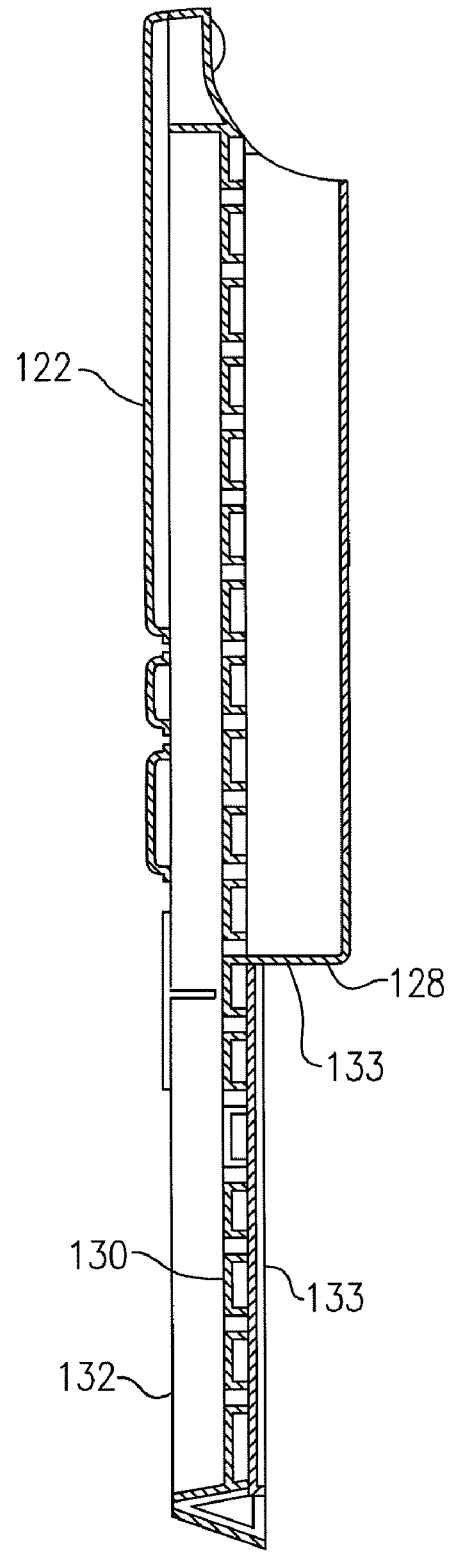
FIG. 17 is a cross-sectional view of the tray (with some cross hatching omitted for clarity of illustration)
Figure 18:
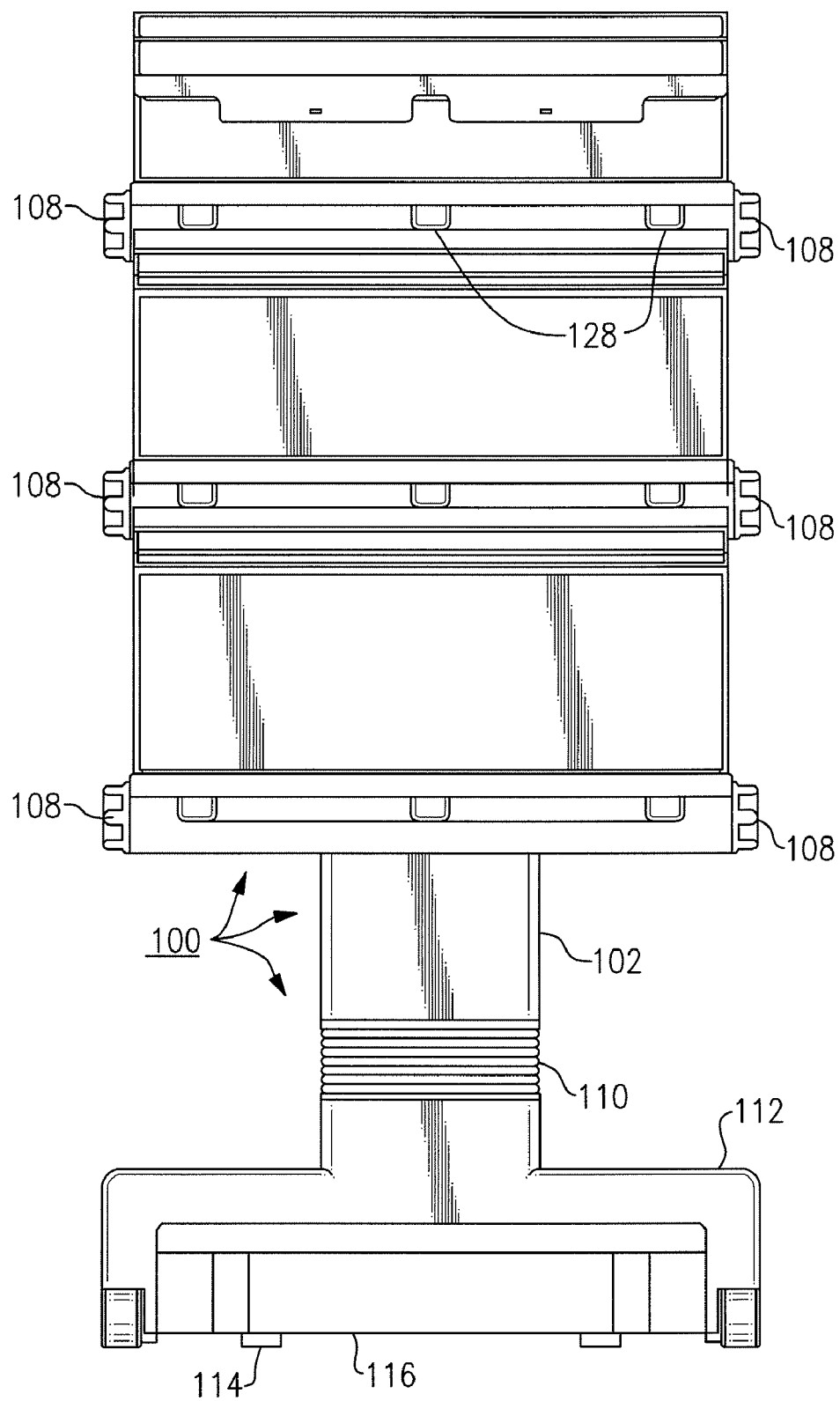
FIG. 18 is an orthographic front view of the first embodiment rack with the trays in place.
Figure 19:
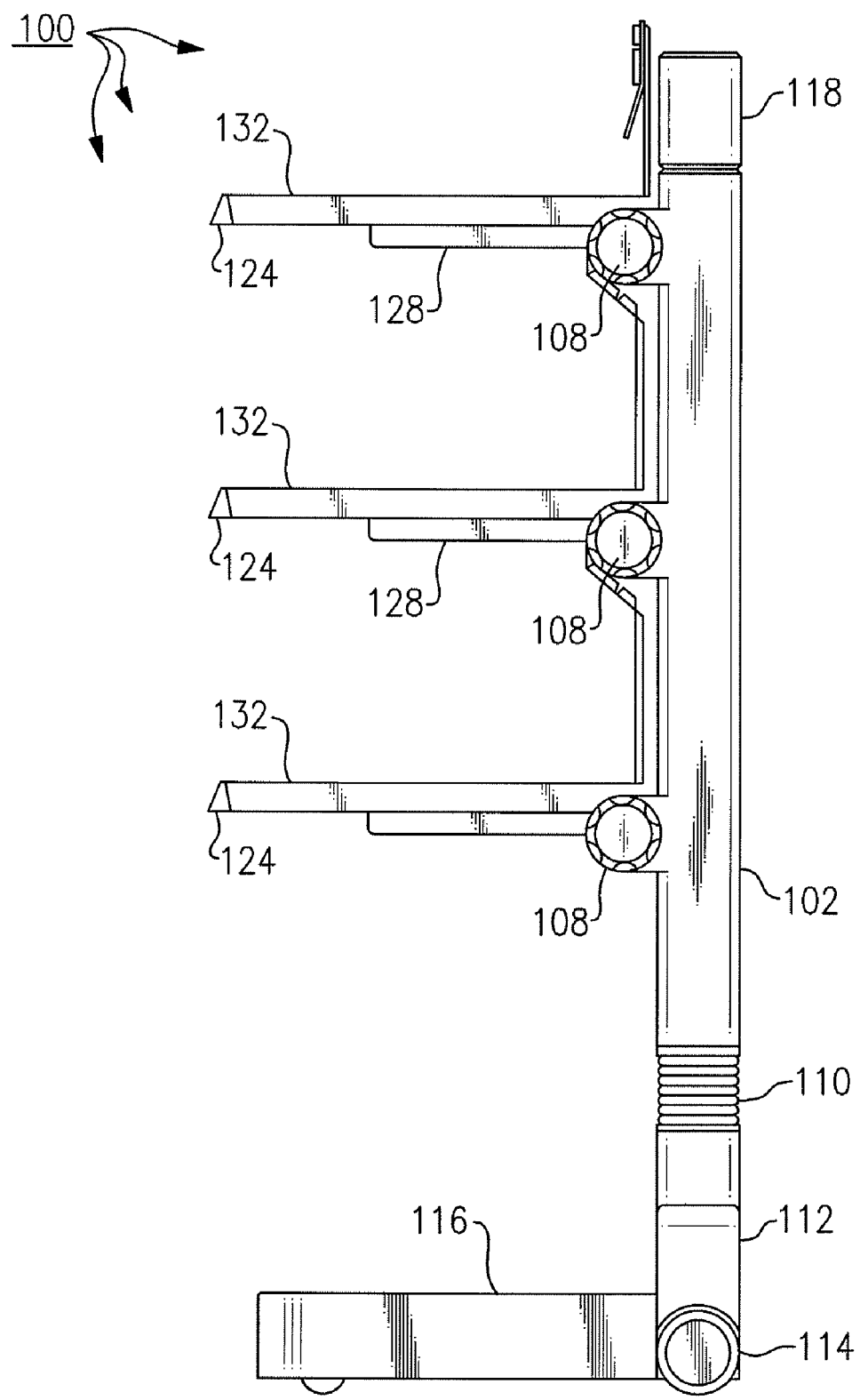
FIG. 19 is an orthographic side view of the first embodiment rack with its trays in place.
Figure 20:
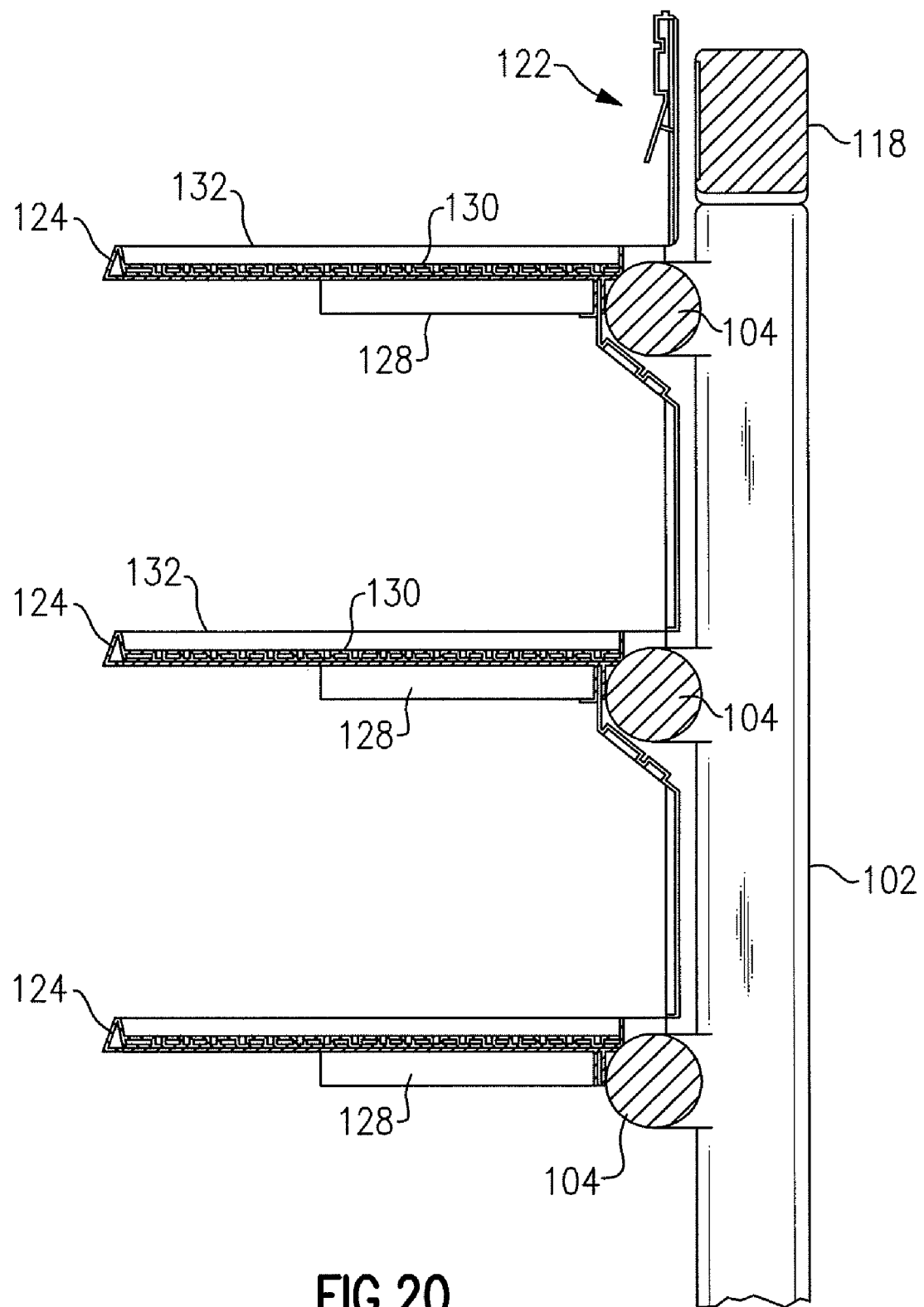
FIG. 20 is partial cross-sectional view of the first embodiment rack with the trays in place.

FIG. 11 shows rack 100 with its rack support braces 104, associated sets of arms 106 and lighted trays 120, 122 at an intermediate angular position in between fully up and fully down. FIGS. 13, 16, 18 and 19 show some preferred, exemplary dimensions and proportions for certain dimensions of rack 100.

DEFINITIONS

The following definitions are provided to facilitate claim interpretation:

Present invention: means at least some embodiments of the present invention; references to various feature(s) of the "present invention" throughout this document do not mean that all claimed embodiments or methods include the referenced feature(s).

First, second, third, etc. ("ordinals"): Unless otherwise noted, ordinals only serve to distinguish or identify (e.g., various members of a group); the mere use of ordinals implies neither a consecutive numerical limit nor a serial limitation.

Mechanically connected: Includes both direct mechanical connections, and indirect mechanical connections made through intermediate components; includes rigid mechanical connections as well as mechanical connection that allows for relative motion between the mechanically connected components; includes, but is not limited, to welded connections, solder connections, connections by fasteners (for example, nails, bolts, screws, nuts, hook-and-loop fasteners, knots, rivets, force fit connections, friction fit connections, connections secured by engagement added by gravitational forces, quick-release connections, pivoting or rotatable connections, slidable mechanical connections and/or magnetic connections.

Light/Light source: unless otherwise clearly indicated by context, light means electromagnetic radiation having wavelengths in the visible light and/or UV range.

Translucent: means at least substantially translucent and/or transparent.

To the extent that the definitions provided above are consistent with ordinary, plain, and accustomed meanings (as generally shown by documents such as dictionaries and/or technical lexicons), the above definitions shall be considered supplemental in nature. To the extent that the definitions provided above are inconsistent with ordinary, plain, and accustomed meanings (as generally shown by documents such as dictionaries and/or technical lexicons), the above definitions shall control. If the definitions provided above are broader than the ordinary, plain, and accustomed meanings in some aspect, then the above definitions shall be considered to broaden the claim accordingly.

To the extent that a patentee may act as its own lexicographer under applicable law, it is hereby further directed that all words appearing in the claims section, except for the above-defined words, shall take on their ordinary, plain, and accustomed meanings (as generally shown by documents such as dictionaries and/or technical lexicons), and shall not be considered to be specially defined in this specification. In the situation where a word or term used in the claims has more than one alternative ordinary, plain and accustomed meaning, the broadest definition that is consistent with technological feasibility and not directly inconsistent with the specification shall control.

Unless otherwise explicitly provided in the claim language, steps in method steps or process claims need only be performed in the same time order as the order the steps are recited in the claim only to the extent that impossibility or extreme feasibility problems dictate that the recited step order (or portion of the recited step order) be used. This broad interpretation with respect to step order is to be used regardless of whether the alternative time ordering(s) of the claimed steps is particularly mentioned or discussed in this document.

What is claimed is:

1. An operating room rack system for holding surgical instruments comprising:
    a rack assembly comprising
        a base;
        at least one vertical support sub-assembly mechanically connected to said base and extending upwardly from said base, and
        a first set of arm(s) comprising at least three arm, with the first set of arm(s) extending from said vertical support sub-assembly wherein each arm of the first set of arms defines an interior space; and each arm of the first set of arm(s) comprises mounting hardware shaped and sized to accommodate a light source within its respective interior space;
    a first light source secured by said mounting hardware, wherein said first light source irradiates at least UV wavelength radiation with sufficient intensity to inhibit bacterial growth on surgical instruments;
    a rack support brace mechanically connected to said vertical support sub-assembly, with said first set of arm(s) being mechanically connected to said rack support brace, and said rack support brace being rotatable about a substantially horizontal rotation axis between at least an up position where said first set of arm(s) extend in a substantially horizontal direction and a down position where said first set of arm(s) extend in a substantially vertical direction; and
    a first tray unit adapted to be detachably attachable to said first set of arm(s) and adapted so that so that when said first tray unit is detachably attached to said first set of arm(s), said first tray unit will remain in a sterile condition even when said first set of arms is not maintained in a sterile condition;
    wherein the first tray unit defines a first set of recess(es) with the first set of recesses being sized, shaped, structured and/or located to engage with the first set of arm(s) wherein the first tray unit comprises an upper tray top member and a lower tray top member; the first set of recess(es) is defined in the lower tray top member; and each arm of the first set of arm(s) is sized, shaped, located and/or structured to be respectively inserted between a recess of the first set of recess(es) and the upper tray top member to form the detachable attachment between the first tray unit and the first set of arm(s).

2. The system of claim 1 wherein said lower tray top member is made of material that is translucent with respect to light.

3. The system of claim 1 wherein said first tray unit further comprises louvers structured and located to allow the passage of light.

4. The system of claim 1 wherein said first light source irradiates at least visible light wavelength radiation with sufficient intensity to provide for visibility in low light conditions.

5. The system of claim 1 further comprising a second tray unit, wherein:
    said rack assembly further comprises a second set of arm(s) comprising at least one arm, with said second set of arm(s) extending from said vertical support sub-assembly at a position lower than said first set of arm(s);
    said second tray unit is adapted to be detachably attachable to said second set of arm(s);
    said first and second sets of arm(s) are located and positioned so that when said first tray unit is detachably attached to said first set of arm(s) and said second tray unit is detachably attached to said second set of arm(s) then light from said light source will irradiate said second tray unit; and wherein the second tray unit defines a second set of recess(es) with the second set of recesses being sized, shaped, structured and/or located to engage with the second set of arm(s) to form the detachable attachment between the second tray unit and the second set of arm(s).

6. The system of claim 1 wherein:
said vertical support sub-assembly comprises a substantially planar front surface defining a front plane, front direction and a back direction; and
said first set of arm(s) are located substantially along the front plane when they are in the down position.

7. The system of claim 1 further comprising a header, wherein:
said vertical support sub-assembly defines a top surface; and
said header is mechanically connected to said vertical support at the top surface.

8. The system of claim 1 wherein said first tray unit is adapted to be disposable.

9. A rack assembly for holding medical instruments, the assembly comprising:
a base;
a first vertical support member;
a first set of arms comprising a plurality of first arms;
a first set light sources comprising a plurality of first light sources;
a first tray unit;
a second set of arms comprising a plurality of second arms; and
a second tray unit;
wherein:
the first vertical support member is mechanically connected to the base;
the first set of arms is rotatably mechanically connected to the first vertical support member so that the first set of arms is rotatable between a tray-supporting position wherein the first set of arms extend in a substantially horizontal direction and a storage position wherein the first set of arms extend downwardly in a substantially vertical direction; the second set of arms is rotatably mechanically connected to the first vertical support member so that the second set of arms is rotatable between a tray-supporting position and a storage position;
each first arm of the first set of arms defines an interior space;
the first light sources of the first set of light sources are respectively located within and respectively mechanically connected to the interior spaces each first arm of the first set of arms wherein said first light source irradiates at least UV wavelength radiation with sufficient intensity to inhibit bacterial growth on surgical instruments;
the first tray unit defines a plurality of first recesses;
the first arms of the first set of arms respectively engage with the first recesses of the plurality of first recesses to form a detachable attachment between the first tray unit and the first set of arms;
the second tray unit defines a plurality of second recesses;
the second arms of the second set of arms respectively engage with the second recesses of the plurality of second recesses to form a detachable attachment between the second tray unit and the second set of arms; and
the first set of light sources, the first set of arms, the first tray unit, the second tray unit and the second set of arms are located, sized, shaped and/or structured so that light from the first set of light sources will be incident of the second tray unit when the first tray units is detachably attached to the first set of arms and the second tray unit is detachably attached to the second set of arms.

10. The assembly of claim 9 wherein the first tray unit includes a translucent portion located so that light from the first set of light sources pass through the translucent portion as the light travels from the first set of light sources to the second tray unit.

\* \* \* \* \*

UNITED STATES PATENT AND TRADEMARK OFFICE
Certificate

Patent No. 8,074,815 B2                                                                 Patented: December 13, 2011

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Robert Gerstner, Hollow, NY (US).

Signed and Sealed this Twelfth Day of June 2012.

DARNELL JAYNE
*Supervisory Patent Examiner*
Art Unit 3637
Technology Center 3600